US008568985B2

(12) United States Patent
Sukumar et al.

(10) Patent No.: US 8,568,985 B2
(45) Date of Patent: Oct. 29, 2013

(54) BREAST ENDOTHELIAL CELL EXPRESSION PATTERNS

(75) Inventors: Saraswati Sukumar, Columbia, MD (US); Stephen L. Madden, Sudbury, MA (US)

(73) Assignees: Genzyme Corporation, Framingham, MA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/176,222

(22) Filed: Jul. 5, 2011

(65) Prior Publication Data

US 2011/0262350 A1    Oct. 27, 2011

Related U.S. Application Data

(63) Continuation of application No. 12/269,418, filed on Nov. 12, 2008, now abandoned, which is a continuation of application No. 10/551,217, filed as application No. PCT/US2004/009704 on Mar. 31, 2004, now abandoned.

(60) Provisional application No. 60/458,960, filed on Apr. 1, 2003.

(51) Int. Cl.
*C12Q 1/68* (2006.01)
*G01N 33/574* (2006.01)

(52) U.S. Cl.
USPC .......................................... 435/6.14; 435/7.23

(58) Field of Classification Search
None
See application file for complete search history.

(56) References Cited

U.S. PATENT DOCUMENTS

| 6,811,776 B2 | 11/2004 | Kale et al. |
| 6,855,554 B2 | 2/2005 | Fritsche et al. |
| 2005/0249666 A1 | 11/2005 | Nakamura et al. |

FOREIGN PATENT DOCUMENTS

| WO | 01/98359 A2 | 12/2001 |
| WO | 02/059377 A2 | 8/2002 |
| WO | 02/079492 A2 | 10/2002 |
| WO | WO 03/070979 A2 * | 8/2003 |

OTHER PUBLICATIONS

Hugo Gene Nomenclature Committee, Gene Symbol Report for SNAI1, printed Nov. 17, 2012.*
Adapt, The Paterson Institute for Cancer Research website information for SNAI1 on gene chips, printed Nov. 17, 2012.*
Nacht et al (Cancer Research, 1999, 59:5464-5470).*
K. Fukutome, Database WPI, XP002452020, "Novel Use of Endothelial Cell Specific Protein C. Receptor as Marker for Determining Breast Cancer," Feb. 13, 2003, Abstract only.
M. Schmid et al., "Insulin-Like Growth Factor Binding Protein-3 is Overexpressed in Endothelial Cells of Mouse Breast Tumor Vessels," Int. J. Cancer: 103, 577-586 (2003).
D. Porter et al., "A Sage (Serial Analysis of Gene Expression) View of Breast Tumor Progression." Cancer Research 61, 5697-5701, Aug. 1, 2001.
H. Hermeking, Ph.D. "Serial Analysis of Gene Expression and Cancer," Current Opinion in Oncology, vol. 15, No. 1, pp. 44-49, Jan. 2003.
T. Takafuta et al., "A New Member of the LIM Protein Family Binds to Filamin B and Localizes at Stress Fibers," The Journal of Biological Chemistry, Apr. 4, 2003, vol. 278, No. 14, pp. 12175-12181, Dec. 20, 2002.
B. Parker, "Alternations in Vascular Gene Expression in Invasive Breast Carcinoma," Cancer Research 64, pp. 7857-7866, Nov. 1, 2004.
Database OMIM (Online), "Heat-Shock 70kD Protein 1A; HSPA1," Johns Hopkins University, 2009, XP002521012 retrieved from NCBI, Database accession No. 140550.
S. E. Conroy et al., "Do Heat Shock Proteins Have a Role in Breast Cancer?" British Journal of Cancer, Sep. 1996, vol. 74, No. 5, pp. 717-721.
V.Z. Volloch et al., "Oncogenic Potential of Hsp72," Oncogene, Jun. 17, 1999, vol. 18, No. 24, pp. 3648-3651.
EPO Search Report issued in corresponding European Application No. 09154001.3 dated May 6, 2009.
Notice of Reasons for Rejection dispatched May 13, 2010 in Japanese Application No. 2006-509475 and English Translation thereof.
Notice of Reasons for Rejection dispatched Dec. 6, 2010 in Japanese Application No. 2006-509475 and English Translation thereof.
Briggs et al., "Transcriptional upregulation of SPARC, in response to c-Jun overexpression, contributes to increased motility and invasion of MCF7 breast cancer cells," Oncogene, 2002, vol. 21, No. 46, p. 7077-7091.
Stedman's medical dictionary, 25th ed., 1990, p. 1029-1030, and p. 1652-1653.
Korkola et al., 2005 Oncogene, 24: 5101-5107.
Bellahcene et al, 1995, Amer J Pathol, 146(1): 95-100.

* cited by examiner

*Primary Examiner* — Laura B Goddard
(74) *Attorney, Agent, or Firm* — Banner & Witcoff, Ltd

(57) ABSTRACT

To gain a better understanding of breast tumor angiogenesis, breast endothelial cells (ECs) were isolated and evaluated for gene expression patterns. When transcripts from breast ECs derived from normal and malignant breast tissues were compared, genes that were specifically elevated in tumor-associated breast endothelium were revealed. These results confirm that neoplastic and normal endothelium in human breast are distinct at the molecular level, and have significant implications for the development of anti-angiogenic therapies in the future.

13 Claims, No Drawings

BREAST ENDOTHELIAL CELL EXPRESSION PATTERNS

TECHNICAL FIELD OF THE INVENTION

This invention is related to the area of angiogenesis and anti-angiogenesis. In particular, it relates to genes which are characteristically expressed in breast tumor endothelial cells.

BACKGROUND OF THE INVENTION

To date, global gene expression profiles from endothelial cell-specific populations is limited to normal and tumorigenic colon tissue [St Croix, 2000]. There is a need in the art for analysis of endothelial cells from other tissue, so that diagnostic and therapeutic agents for non-colonic tumors can be developed.

SUMMARY OF THE INVENTION

According to one embodiment of the invention a method is provided to aid in diagnosing breast tumors. An expression product (protein or RNA) of at least one gene in a first breast tissue sample suspected of being neoplastic is detected. The at least one gene is selected from the group consisting of hypothetical protein DKFZp434G171; heat shock 70 kDa protein 1A; jagged 1 (Alagille syndrome); cyclin-dependent kinase 3; 6-phosphogluconolactonase; likely homolog of rat and mouse retinoid-inducible serine carboxypeptidase; plasmalemma vesicle associated protein; NADH:ubiquinone oxidoreductase MLRQ subunit homolog; HIF-1 responsive RTP801; ribosomal protein L27; secreted protein, acidic, cysteine-rich (osteonectin); hexokinase 1; ribosomal protein L13a; collagen, type IV, alpha 1; insulin-like growth factor binding protein 7; collagen, type III, alpha 1 (Ehlers-Danlos syndrome type IV, autosomal dominant); heat shock 10 kDa protein 1 (chaperonin 10); calcium channel, voltage-dependent, alpha 1H subunit; CD9 antigen (p24); TEM17; TEM13; Thy-1 cell surface antigen; Tax interaction protein 1; dysferlin, limb girdle muscular dystrophy 2B (autosomal recessive); hypothetical protein MGC34648; putative translation initiation factor; insulin-like growth factor binding protein 4; matrix metalloproteinase 9 (gelatinase B, 92 kDa gelatinase, 92 kDa type IV collagenase); heterogeneous nuclear ribonucleoprotein R; bHLH factor Hes4; collagen, type VI, alpha 2; T-box 2; glyceraldehyde-3-phosphate dehydrogenase; G protein-coupled receptor 4; collagen, type I, alpha 1; ras-related C3 botulinum toxin substrate 1 (rho family, small GTP binding protein Rac1); ribosomal protein, large, P1; TEM10, COL1A2 involved in tissue remodeling; heat shock 70 kDa protein 8; KIAA0152 gene product; Ca2+-promoted Ras inactivator; serine/arginine repetitive matrix 2; hypoxia-inducible factor 1, alpha subunit (basic helix-loop-helix transcription factor); benzodiazapine receptor (peripheral); ectonucleoside triphosphate diphosphohydrolase 1; heparan sulfate proteoglycan 2 (perlecan); fibromodulin; hairy/enhancer-of-split related with YRPW motif 1; collagen, type V, alpha 3; hairy/enhancer-of-split related with YRPW motif-like; hypothetical protein MGC2731; amino-terminal enhancer of split; mitogen-activated protein kinase 9; regulator of G-protein signalling 5; prothymosin, alpha (gene sequence 28); tubulin, beta, 2; protease, serine, 23; hypothetical protein FLJ20898; calpain 1, (mu/I) large subunit; interferon, alpha-inducible protein (clone IFI-6-16); ESTs, Weakly similar to T25031 hypothetical protein T20D3.3—*Caenorhabditis elegans* [*C. elegans*]; major histocompatibility complex, class I, C; hypoxia up-regulated 1; complement component 4B; prefoldin 2; cytoskeleton-associated protein 1; Rho GTPase activating protein 4; *Homo sapiens* clone FLC1492 PRO3121 mRNA, complete cds; transducin-like enhancer of split 2 (E(sp1) homolog, *Drosophila*); ribosomal protein L37; hypothetical protein MGC4677; ESTs, Highly similar to MT1A_HUMAN METALLOTHIONEIN-IA (MT-1A) [*H. sapiens*]; TEM11, nidogen (enactin); guanine nucleotide binding protein (G protein), gamma 5; matrix Gla protein; heat shock 105ld); GNAS complex locus; *Homo sapiens* cDNA FLJ11658 fis, clone HEMBA1004577; H19, imprinted maternally expressed untranslated mRNA; protein tyrosine phosphatase type IVA, member 3; snail homolog 1 (*Drosophila*); integrin-binding sialoprotein (bone sialoprotein, bone sialoprotein II); tissue inhibitor of metalloproteinase 1 (erythroid potentiating activity, collagenase inhibitor); peptidylprolyl isomerase B (cyclophilin B); MARCKS-like protein; FAST kinase; protease, serine, 11 (IGF binding); beta-2-microglobulin; delta sleep inducing peptide, immunoreactor; collagen, type IV, alpha 2; immediate early response 3; cadherin 5, type 2, VE-cadherin (vascular epithelium); RGC32 protein; guanylate cyclase 1, soluble, beta 3; major histocompatibility complex, class I, B; ribonuclease, RNase A family, 1 (pancreatic); collagen, type XVIII, alpha 1; v-jun sarcoma virus 17 oncogene homolog (avian); *Homo sapiens* mRNA; cDNA DKFZp686G1610 (from clone DKFZp686G1610); nucleolin; lectin, galactoside-binding, soluble, 3 binding protein; Lysosomal-associated multispanning membrane protein-5; ribosomal protein S16; guanine nucleotide binding protein (G protein), gamma 12; serine (or cysteine) proteinase inhibitor, Glade E (nexin, plasminogen activator inhibitor type 1), member 1; biglycan; DnaJ (Hsp40) homolog, subfamily B, member 1; tumor rejection antigen (gp96) 1; interferon, alpha-inducible protein (clone IFI-15K); solute carrier family 21 (prostaglandin transporter), member 2; CD74 antigen (invariant polypeptide of major histocompatibility complex, class II antigen-associated); serum/glucocorticoid regulated kinase; mitogen-activated protein kinase; receptor (calcitonin) activity modifying protein 3; sema domain, immunoglobulin domain (Ig); benzodiazapine receptor (peripheral)—mitochondrial; C1 domain-containing phosphatase & tensin-like; and Notch homolog 3 (*Drosophila*). Expression of the at least one gene in the first breast tissue sample is compared to expression of the at least one gene in a second breast tissue sample which is normal. Increased expression of the at least one gene in the first breast endothelial tissue sample relative to the second tissue sample identifies the first breast tissue sample as likely to be neoplastic.

According to another embodiment of the invention a method is provided of treating a breast tumor. Cells of the breast tumor are contacted with an antibody. The antibody specifically binds to an extracellular epitope of a protein selected from the group consisting of benzodiazepine receptor (peripheral); cadherin 5, type 2, VE-cadherin (vascular epithelium); calcium channel, voltage-dependent, alpha 1H subunit; CD74 antigen (invariant polypeptide of major histocompatibility complex, class II antigen-associated); CD9 antigen (p24); dysferlin, limb girdle muscular dystrophy 2B (autosomal recessive); ectonucleoside triphosphate diphosphohydrolase 1; G protein-coupled receptor 4; hypothetical protein FLJ20898; hypoxia up-regulated 1; immediate early response 3; interferon, alpha-inducible protein (clone IFI-6-16); jagged 1 (Alagille syndrome); KIAA0152 gene product; Lysosomal-associated multispanning membrane protein-5; major histocompatibility complex, class I, B; major histocompatibility complex, class I, C; NADH:ubiquinone oxidoreductase MLRQ subunit homolog; Notch homolog 3

(*Drosophila*); plasmalemma vesicle associated protein; solute carrier family 21 (prostaglandin transporter), member 2; TEM13, Thy-1 cell surface antigen; receptor (calcitonin) activity modifying protein 3; sema domain, immunoglobulin domain (Ig); benzodiazapine receptor (peripheral)—mitochondrial; and TEM17. Immune destruction of cells of the breast tumor is thereby triggered.

According to still another embodiment of the invention a method is provided for identifying a test compound as a potential anti-cancer or anti-breast tumor drug. A test compound is contacted with a cell which expresses at least one gene selected from the group consisting of: hypothetical protein DKFZp434G171; heat shock 70 kDa protein 1A; jagged 1 (Alagille syndrome); cyclin-dependent kinase 3; 6-phosphogluconolactonase; likely homolog of rat and mouse retinoid-inducible serine carboxypeptidase; plasmalemma vesicle associated protein; NADH:ubiquinone oxidoreductase MLRQ subunit homolog; HIF-1 responsive RTP801; ribosomal protein L27; secreted protein, acidic, cysteine-rich (osteonectin); hexokinase 1; ribosomal protein L13a; collagen, type IV, alpha 1; insulin-like growth factor binding protein 7; collagen, type III, alpha 1 (Ehlers-Danlos syndrome type IV, autosomal dominant); heat shock 10 kDa protein 1 (chaperonin 10); calcium channel, voltage-dependent, alpha 1H subunit; CD9 antigen (p24); TEM17; TEM13, Thy-1 cell surface antigen; Tax interaction protein 1; dysferlin, limb girdle muscular dystrophy 2B (autosomal recessive); hypothetical protein MGC34648; putative translation initiation factor; insulin-like growth factor binding protein 4; matrix metalloproteinase 9 (gelatinase B, 92 kDa gelatinase, 92 kDa type IV collagenase); heterogeneous nuclear ribonucleoprotein R; bHLH factor Hes4; collagen, type VI, alpha 2; T-box 2; glyceraldehyde-3-phosphate dehydrogenase; G protein-coupled receptor 4; collagen, type I, alpha 1; ras-related C3 botulinum toxin substrate 1 (rho family, small GTP binding protein Rac1); ribosomal protein, large, P1; TEM10, COL1A2 involved in tissue remodeling; heat shock 70 kDa protein 8; KIAA0152 gene product; Ca2+-promoted Ras inactivator; serine/arginine repetitive matrix 2; hypoxia-inducible factor 1, alpha subunit (basic helix-loop-helix transcription factor); benzodiazapine receptor (peripheral); ectonucleoside triphosphate diphosphohydrolase 1; heparan sulfate proteoglycan 2 (perlecan); fibromodulin; hairy/enhancer-of-split related with YRPW motif 1; collagen, type V, alpha 3; hairy/enhancer-of-split related with YRPW motif-like; hypothetical protein MGC2731; amino-terminal enhancer of split; mitogen-activated protein kinase 9; regulator of G-protein signalling 5; prothymosin, alpha (gene sequence 28); tubulin, beta, 2; protease, serine, 23; hypothetical protein FLJ20898; calpain 1, (mu/I) large subunit; interferon, alpha-inducible protein (clone IFI-6-16); ESTs, Weakly similar to T25031 hypothetical protein T20D3.3—*Caenorhabditis elegans [C. elegans]*; major histocompatibility complex, class I, C; hypoxia up-regulated 1; complement component 4B; prefoldin 2; cytoskeleton-associated protein 1; Rho GTPase activating protein 4; *Homo sapiens* clone FLC1492 PRO3121 mRNA, complete cds; transducin-like enhancer of split 2 (E(sp1) homolog, *Drosophila*); ribosomal protein L37; hypothetical protein MGC4677; ESTs, Highly similar to MT1A_HUMAN METALLOTHIONEIN-IA (MT-1A) [*H. sapiens*]; TEM11, nidogen (enactin); guanine nucleotide binding protein (G protein), gamma 5; matrix Gla protein; heat shock 105 kD; GNAS complex locus; *Homo sapiens* cDNA FLJ11658 fis, clone HEMBA1004577; H19, imprinted maternally expressed untranslated mRNA; protein tyrosine phosphatase type WA, member 3; snail homolog 1 (*Drosophila*); integrin-binding sialoprotein (bone sialoprotein, bone sialoprotein II); tissue inhibitor of metalloproteinase 1 (erythroid potentiating activity, collagenase inhibitor); peptidylprolyl isomerase B (cyclophilin B); MARCKS-like protein; FAST kinase; protease, serine, 11 (IGF binding); beta-2-microglobulin; delta sleep inducing peptide, immunoreactor; collagen, type IV, alpha 2; immediate early response 3; cadherin 5, type 2, VE-cadherin (vascular epithelium); RGC32 protein; guanylate cyclase 1, soluble, beta 3; major histocompatibility complex, class I, B; ribonuclease, RNase A family, 1 (pancreatic); collagen, type XVIII, alpha 1; v-jun sarcoma virus 17 oncogene homolog (avian); *Homo sapiens* mRNA; cDNA DKFZp686G1610 (from clone DKFZp686G1610); nucleolin; lectin, galactoside-binding, soluble, 3 binding protein; Lysosomal-associated multispanning membrane protein-5; ribosomal protein S16; guanine nucleotide binding protein (G protein), gamma 12; serine (or cysteine) proteinase inhibitor, Glade E (nexin, plasminogen activator inhibitor type 1), member 1; biglycan; DnaJ (Hsp40) homolog, subfamily B, member 1; tumor rejection antigen (gp96) 1; interferon, alpha-inducible protein (clone IFI-15K); solute carrier family 21 (prostaglandin transporter), member 2; CD74 antigen (invariant polypeptide of major histocompatibility complex, class II antigen-associated); serum/glucocorticoid regulated kinase; mitogen-activated protein kinase; receptor (calcitonin) activity modifying protein 3; sema domain, immunoglobulin domain (Ig); benzodiazapine receptor (peripheral)—mitochondrial; C1 domain-containing phosphatase & tensin-like; and Notch homolog 3 (*Drosophila*). An expression product of the at least one gene is monitored. The test compound is identified as a potential anti-cancer drug if it decreases the expression of the at least one gene.

Still another embodiment of the invention is a method to induce an immune response to a breast tumor. A protein or nucleic acid encoding a protein is administered to a mammal, preferably a human. The protein is selected from the group consisting of: hypothetical protein DKFZp434G171; heat shock 70 kDa protein 1A; jagged 1 (Alagille syndrome); cyclin-dependent kinase 3; 6-phosphogluconolactonase; likely homolog of rat and mouse retinoid-inducible serine carboxypeptidase; plasmalemma vesicle associated protein; NADH:ubiquinone oxidoreductase MLRQ subunit homolog; HIF-1 responsive RTP801; ribosomal protein L27; secreted protein, acidic, cysteine-rich (osteonectin); hexokinase 1; ribosomal protein L13a; collagen, type IV, alpha 1; insulin-like growth factor binding protein 7; collagen, type III, alpha 1 (Ehlers-Danlos syndrome type IV, autosomal dominant); heat shock 10 kDa protein 1 (chaperonin 10); calcium channel, voltage-dependent, alpha 1H subunit; CD9 antigen (p24); TEM17; TEM13, Thy-1 cell surface antigen; Tax interaction protein 1; dysferlin, limb girdle muscular dystrophy 2B (autosomal recessive); hypothetical protein MGC34648; putative translation initiation factor; insulin-like growth factor binding protein 4; matrix metalloproteinase 9 (gelatinase B, 92 kDa gelatinase, 92 kDa type IV collagenase); heterogeneous nuclear ribonucleoprotein R; bHLH factor Hes4; collagen, type VI, alpha 2; T-box 2; glyceraldehyde-3-phosphate dehydrogenase; G protein-coupled receptor 4; collagen, type I, alpha 1; ras-related C3 botulinum toxin substrate 1 (rho family, small GTP binding protein Rac1); ribosomal protein, large, P1; TEM10, COL1A2 involved in tissue remodeling; heat shock 70 kDa protein 8; KIAA0152 gene product; Ca2+-promoted Ras inactivator; serine/arginine repetitive matrix 2; hypoxia-inducible factor 1, alpha subunit (basic helix-loop-helix transcription factor); benzodiazapine receptor (peripheral); ectonucleoside triphosphate diphosphohydrolase 1; heparan sulfate proteoglycan 2 (perlecan); fibromodulin; hairy/enhancer-of-split related with YRPW motif 1; collagen, type V, alpha 3; hairy/enhancer-of-split related with YRPW motif-like; hypothetical protein MGC2731; amino-terminal enhancer of split; mitogen-activated protein kinase 9; regulator of G-protein signalling 5; prothymosin, alpha (gene sequence 28); tubulin, beta, 2; protease, serine, 23; hypothetical protein FLJ20898; calpain 1, (mu/I) large subunit; interferon, alpha-inducible protein (clone IFI-6-16); ESTs, Weakly similar to T25031 hypothetical protein T20D3.3—*Caenorhabditis elegans [C. elegans]*; major histocompatibility complex, class I, C; hypoxia up-regulated 1; complement component 4B; prefoldin 2; cytoskeleton-associated protein 1; Rho GTPase activating protein 4; *Homo sapiens* clone FLC1492 PRO3121 mRNA, complete cds; transducin-like enhancer of split 2 (E(sp1) homolog, *Drosophila*); ribosomal protein L37; hypothetical protein MGC4677; ESTs, Highly similar to MT1A_HUMAN METALLOTHIONEIN-IA (MT-1A) [*H. sapiens*]; TEM11, nidogen (enactin); guanine nucleotide binding protein (G protein), gamma 5; matrix Gla protein; heat shock 1051d); GNAS complex locus; *Homo sapiens* cDNA FLJ11658 fis, clone HEMBA1004577; H19, imprinted maternally expressed untranslated mRNA; protein tyrosine phosphatase type IVA, member 3; snail homolog 1 (*Drosophila*); integrin-binding sialoprotein (bone sialoprotein, bone sialoprotein II); tissue inhibitor of metalloproteinase 1 (erythroid potentiating activity, collagenase inhibitor); peptidylprolyl isomerase B (cyclophilin B); MARCKS-like protein; FAST kinase; protease, serine, 11 (IGF binding); beta-2-microglobulin; delta sleep inducing peptide, immunoreactor; collagen, type IV, alpha 2; immediate early response 3; cadherin 5, type 2, VE-cadherin (vascular epithelium); RGC32 protein; guanylate cyclase 1, soluble, beta 3; major histocompatibility complex, class I, B; ribonuclease, RNase A family, 1 (pancreatic); collagen, type XVIII, alpha 1; v-jun sarcoma virus 17 oncogene homolog (avian); *Homo sapiens* mRNA; cDNA DKFZp686G1610 (from clone DKFZp686G1610); nucleolin; lectin, galactoside-binding, soluble, 3 binding protein; Lysosomal-associated multispanning membrane protein-5; ribosomal protein S16; guanine nucleotide binding protein (G protein), gamma 12; serine (or cysteine) proteinase inhibitor, Glade E (nexin, plasminogen activator inhibitor type 1), member 1; biglycan; DnaJ (Hsp40) homolog, subfamily B, member 1; tumor rejection antigen (gp96) 1; interferon, alpha-inducible protein (clone IFI-15K); solute carrier family 21 (prostaglandin transporter), member 2; CD74 antigen (invariant polypeptide of major histocompatibility complex, class II antigen-associated); serum/glucocorticoid regulated kinase; mitogen-activated protein kinase; receptor (calcitonin) activity modifying protein 3; sema domain, immunoglobulin domain (Ig); benzodiazapine receptor (peripheral)—mitochondrial; C1 domain-containing phosphatase & tensin-like; and Notch homolog 3 (*Drosophila*). An immune response to the protein is thereby induced.

The present invention thus provides the art with methods of diagnosing and treating breast tumors.

DETAILED DESCRIPTION OF THE INVENTION

Using SAGE (Serial Analysis of Gene Expression) profiling, the present inventors were able to identify previously unrecognized, angiogenesis-specific markers that discriminate between non-proliferative and pathologic endothelial cells. In addition, a set of previously identified angiogenesis-specific markers from other tumor types (colon and/or brain) were found to be expressed in breast tumor endothelium as well. We identified 111 human genes that were expressed at significantly higher levels in breast tumor endothelium than in normal breast endothelium. See Table 1. Additional such genes which can be used similarly to the 11 human genes are shown in Table 2. We have named these markers BEMs (breast tumor endothelial markers). BEMs that are expressed in both colon and breast tumor epithelium are identified in Table 3. BEMs that are expressed in both brain and breast tumor epithelium are identified in Table 4. BEMs that are expressed in each of brain, colon, and breast tumor epithelium are identified in Table 5.

TABLE 1

111 Breast Markers

| Unigene ID | Function | OMIMID | Protein |
|---|---|---|---|
| Hs.8728 | hypothetical protein DKFZp434G171 | | CAB61365 |
| Hs.8997 | heat shock 70 kDa protein 1A | 140550 | NP_005336 |
| Hs.91143 | jagged 1 (Alagille syndrome) | 601920 | NP_000205 |
| Hs.100009 | cyclin-dependent kinase 3 | 123828 | |
| Hs.100071 | 6-phosphogluconolactonase | 604951 | NP_036220 |
| Hs.106747 | likely homolog of rat and mouse retinoid-inducible serine carboxypeptidase | | NP_067639 |
| Hs.107125 | plasmalemma vesicle associated protein | | NP_112600 |
| Hs.110024 | NADH:ubiquinone oxidoreductase MLRQ subunit homolog | | NP_064527 |
| Hs.111244 | HIF-1 responsive RTP801 | | NP_061931 |
| Hs.111611 | ribosomal protein L27 | 607526 | NP_000979 |
| Hs.111779 | secreted protein, acidic, cysteine-rich (osteonectin) | 182120 | NP_003109 |
| Hs.118625 | hexokinase 1 | 142600 | NP_277035 |
| Hs.119122 | ribosomal protein L13a | | |
| Hs.119129 | collagen, type IV, alpha 1 | 120130 | NP_001836 |
| Hs.119206 | insulin-like growth factor binding protein 7 | 602867 | NP_001544 |
| Hs.119571 | collagen, type III, alpha 1 (Ehlers-Danlos syndrome type IV, autosomal dominant) | 120180 | NP_000081 |
| Hs.1197 | heat shock 10 kDa protein 1 (chaperonin 10) | 600141 | NP_002148 |
| Hs.122359 | calcium channel, voltage-dependent, alpha 1H subunit | | NP_066921 |
| Hs.1244 | CD9 antigen (p24) | 143030 | NP_001760 |
| Hs.125036 | TEM17 | 606826 | NP_065138 |
| Hs.125359 | TEM13, Thy-1 cell surface antigen | 188230 | NP_006279 |
| Hs.12956 | Tax interaction protein 1 | | NP_055419 |
| Hs.143897 | dysferlin, limb girdle muscular dystrophy 2B (autosomal recessive) | 603009 | NP_003485 |

TABLE 1-continued

111 Breast Markers

| Unigene ID | Function | OMIMID | Protein |
|---|---|---|---|
| Hs.146360 | hypothetical protein MGC34648 | | NP_689873 |
| Hs.150580 | putative translation initiation factor | | NP_005792 |
| Hs.1516 | insulin-like growth factor binding protein 4 | 146733 | NP_001543 |
| Hs.151738 | matrix metalloproteinase 9 (gelatinase B, 92 kDa gelatinase, 92 kDa type IV collagenase) | 120361 | NP_004985 |
| Hs.15265 | heterogeneous nuclear ribonucleoprotein R | 607201 | NP_005817 |
| Hs.154029 | bHLH factor Hes4 | | NP_066993 |
| Hs.159263 | collagen, type VI, alpha 2 | 120240 | NP_001840 |
| Hs.168357 | T-box 2 | 600747 | NP_005985 |
| Hs.169476 | glyceraldehyde-3-phosphate dehydrogenase | 138400 | NP_002037 |
| Hs.17170 | G protein-coupled receptor 4 | 600551 | NP_005273 |
| Hs.172928 | collagen, type I, alpha 1 | 120150 | NP_000079 |
| Hs.173737 | ras-related C3 botulinum toxin substrate 1 (rho family, small GTP binding protein Rac1) | 602048 | |
| Hs.177592 | ribosomal protein, large, P1 | 180520 | |
| Hs.179573 | TEM10, COL1A2 involved in tissue remodeling | 120160 | NP_000080 |
| Hs.180414 | heat shock 70 kDa protein 8 | 600816 | NP_006588 |
| Hs.181418 | KIAA0152 gene product | | NP_055545 |
| Hs.184367 | Ca2+-promoted Ras inactivator | | BAA25464 |
| Hs.197114 | serine/arginine repetitive matrix 2 | 606032 | NP_057417 |
| Hs.197540 | hypoxia-inducible factor 1, alpha subunit (basic helix-loop-helix transcription factor) | 603348 | NP_001521 |
| Hs.202 | benzodiazapine receptor (peripheral) | 109610 | NP_000705 |
| Hs.205353 | ectonucleoside triphosphate diphosphohydrolase 1 | 601752 | NP_001767 |
| Hs.211573 | heparan sulfate proteoglycan 2 (perlecan) | 142461 | NP_005520 |
| Hs.230 | Fibromodulin | 600245 | NP_002014 |
| Hs.234434 | hairy/enhancer-of-split related with YRPW motif 1 | 602953 | NP_036390 |
| Hs.235368 | collagen, type V, alpha 3 | 120216 | NP_056534 |
| Hs.23823 | hairy/enhancer-of-split related with YRPW motif-like | | NP_055386 |
| Hs.240170 | hypothetical protein MGC2731 | | NP_076973 |
| Hs.244 | amino-terminal enhancer of split | 600188 | |
| Hs.246857 | mitogen-activated protein kinase 9 | 602896 | NP_620708 |
| Hs.24950 | regulator of G-protein signalling 5 | 603276 | NP_003608 |
| Hs.250655 | prothymosin, alpha (gene sequence 28) | 188390 | NP_002814 |
| Hs.251653 | tubulin, beta, 2 | 602660 | NP_006079 |
| Hs.25338 | protease, serine, 23 | | |
| Hs.25549 | hypothetical protein FLJ20898 | | NP_078876 |
| Hs.2575 | calpain 1, (mu/l) large subunit | 114220 | NP_005177 |
| Hs.265827 | interferon, alpha-inducible protein (clone IFI-6-16) | 147572 | NP_075011 |
| Hs.267200 | ESTs, Weakly similar to T25031 hypothetical protein T20D3.3 - Caenorhabditis elegans [*C. elegans*] | | |
| Hs.277477 | major histocompatibility complex, class I, C | 142840 | NP_002108 |
| Hs.277704 | hypoxia up-regulated 1 | 601746 | NP_006380 |
| Hs.278625 | complement component 4B | 120820 | NP_000583 |
| Hs.298229 | prefoldin 2 | | NP_036526 |
| Hs.31053 | cytoskeleton-associated protein 1 | 601303 | NP_001272 |
| Hs.3109 | Rho GTPase activating protein 4 | 300023 | NP_001657 |
| Hs.327412 | *Homo sapiens* clone FLC1492 PRO3121 mRNA, complete cds | | |
| Hs.332173 | transducin-like enhancer of split 2 (E(sp1) homolog, *Drosophila*) | 601041 | NP_003251 |
| Hs.337445 | ribosomal protein L37 | 604181 | NP_000988 |
| Hs.337986 | hypothetical protein MGC4677 | | NP_443103 |
| Hs.353882 | ESTs, Highly similar to MT1A_HUMAN METALLOTHIONEIN-IA (MT-1A) [*H. sapiens*] | | |
| Hs.356624 | TEM11, nidogen (enactin) | 131390 | NP_002499 |
| Hs.356668 | guanine nucleotide binding protein (G protein), gamma 5 | 600874 | NP_005265 |
| Hs.365706 | matrix Gla protein | 154870 | NP_000891 |
| Hs.36927 | heat shock 105 Kd | | NP_006635 |
| Hs.374523 | GNAS complex locus | 139320 | NP_536350 |
| Hs.380824 | *Homo sapiens* cDNA FLJ11658 fis, clone HEMBA1004577 | | |
| Hs.406410 | H19, imprinted maternally expressed untranslated mRNA | 103280 | BAB71280 |
| Hs.43666 | protein tyrosine phosphatase type IVA, member 3 | 606449 | NP_116000 |
| Hs.48029 | snail homolog 1 (*Drosophila*) | 604238 | NP_005976 |
| Hs.49215 | integrin-binding sialoprotein (bone sialoprotein, bone sialoprotein II) | 147563 | NP_004958 |
| Hs.5831 | tissue inhibitor of metalloproteinase 1 (erythroid potentiating activity, collagenase inhibitor) | 305370 | NP_003245 |
| Hs.699 | peptidylprolyl isomerase B (cyclophilin B) | 123841 | NP_000933 |
| Hs.75061 | MARCKS-like protein | 602940 | NP_075385 |
| Hs.75087 | FAST kinase | 606965 | NP_079372 |
| Hs.75111 | protease, serine, 11 (IGF binding) | 602194 | NP_002766 |
| Hs.75415 | beta-2-microglobulin | 109700 | NP_004039 |

TABLE 1-continued

111 Breast Markers

| Unigene ID | Function | OMIMID | Protein |
|---|---|---|---|
| Hs.75450 | delta sleep inducing peptide, immunoreactor | 602960 | |
| Hs.75617 | collagen, type IV, alpha 2 | 120090 | NP_001837 |
| Hs.76095 | immediate early response 3 | 602996 | NP_434702 |
| Hs.76206 | cadherin 5, type 2, VE-cadherin (vascular epithelium) | 601120 | NP_001786 |
| Hs.76640 | RGC32 protein | | |
| Hs.77890 | guanylate cyclase 1, soluble, beta 3 | 139397 | NP_000848 |
| Hs.77961 | major histocompatibility complex, class I, B | 142830 | NP_005505 |
| Hs.78224 | ribonuclease, RNase A family, 1 (pancreatic) | 180440 | AAH05324 |
| Hs.78409 | collagen, type XVIII, alpha 1 | 120328 | NP_085059 |
| Hs.78465 | v-jun sarcoma virus 17 oncogene homolog (avian) | 165160 | NP_002219 |
| Hs.7869 | *Homo sapiens* mRNA; cDNA DKFZp686G1610 (from clone DKFZp686G1610) | | |
| Hs.79110 | Nucleolin | 164035 | NP_005372 |
| Hs.79339 | lectin, galactoside-binding, soluble, 3 binding protein | 600626 | NP_005558 |
| Hs.79356 | Lysosomal-associated multispanning membrane protein-5 | 601476 | NP_006753 |
| Hs.80617 | ribosomal protein S16 | 603675 | |
| Hs.8107 | guanine nucleotide binding protein (G protein), gamma 12 | | |
| Hs.82085 | serine (or cysteine) proteinase inhibitor, clade E (nexin, plasminogen activator inhibitor type 1), member 1 | 173360 | NP_000593 |
| Hs.821 | Biglycan | 301870 | NP_001702 |
| Hs.82646 | DnaJ (Hsp40) homolog, subfamily B, member 1 | 604572 | NP_006136 |
| Hs.82689 | tumor rejection antigen (gp96) 1 | 191175 | NP_003290 |
| Hs.833 | interferon, alpha-inducible protein (clone IFI-15K) | 147571 | NP_005092 |
| Hs.83974 | solute carrier family 21 (prostaglandin transporter), member 2 | 601460 | NP_005621 |
| Hs.84298 | CD74 antigen (invariant polypeptide of major histocompatibility complex, class II antigen-associated) | 142790 | NP_004346 |
| Hs.8546 | Notch homolog 3 (*Drosophila*) | 600276 | NP_000426 |

TABLE 2

Additional Tumor Endothelial Markers in Breast

| Unigene ID | Function | OMIMID | Protein |
|---|---|---|---|
| Hs.296323 | serum/glucocorticoid regulated kinase | 602958 | NP_005618 |
| Hs.246857 | mitogen-activated protein kinase | 602896 | NP_620708 |
| Hs.25691 | receptor (calcitonin) activity modifying protein 3 | 605155 | NP_005847 |
| Hs.9598 | sema domain, immunoglobulin domain (Ig) | — | BAB21836 |
| Hs.202 | benzodiazapine receptor (peripheral) - mitochondrial | 109610 | NP_000715 |
| Hs.6147 | C1 domain-containing phosphatase & tensin-like | — | NP_056134 |

TABLE 3

Markers in Colon and Breast Tumor Epithelium

| Unigene ID | Function | OMIMID | Protein |
|---|---|---|---|
| Hs.8997 | heat shock 70 kDa protein 1A | 140550 | NP_005336 |
| Hs.110024 | NADH:ubiquinone oxidoreductase MLRQ subunit homolog | | NP_064527 |
| Hs.111779 | secreted protein, acidic, cysteine-rich (osteonectin) | 182120 | NP_003109 |
| Hs.119129 | collagen, type IV, alpha 1 | 120130 | NP_001836 |
| Hs.119206 | insulin-like growth factor binding protein 7 | 602867 | NP_001544 |
| Hs.119571 | collagen, type III, alpha 1 (Ehlers-Danlos syndrome type IV, autosomal dominant) | 120180 | NP_000081 |
| Hs.1197 | heat shock 10 kDa protein 1 (chaperonin 10) | 600141 | NP_002148 |
| Hs.125036 | TEM17 | 606826 | NP_065138 |
| Hs.125359 | TEM13, Thy-1 cell surface antigen | 188230 | NP_006279 |
| Hs.151738 | matrix metalloproteinase 9 (gelatinase B, 92 kDa gelatinase, 92 kDa type IV collagenase) | 120361 | NP_004985 |
| Hs.159263 | collagen, type VI, alpha 2 | 120240 | NP_001840 |
| Hs.168357 | T-box 2 | 600747 | NP_005985 |
| Hs.172928 | collagen, type I, alpha 1 | 120150 | NP_000079 |
| Hs.179573 | TEM10, COL1A2 involved in tissue remodeling | 120160 | NP_000080 |
| Hs.230 | Fibromodulin | 600245 | NP_002014 |
| Hs.23823 | hairy/enhancer-of-split related with YRPW motif-like | | NP_055386 |
| Hs.24950 | regulator of G-protein signalling 5 | 603276 | NP_003608 |
| Hs.265827 | interferon, alpha-inducible protein (clone IFI-6-16) | 147572 | NP_075011 |

TABLE 3-continued

Markers in Colon and Breast Tumor Epithelium

| Unigene ID | Function | OMIMID | Protein |
|---|---|---|---|
| Hs.327412 | *Homo sapiens* clone FLC1492 PRO3121 mRNA, complete cds | | |
| Hs.337986 | hypothetical protein MGC4677 | | NP_443103 |
| Hs.356624 | TEM11, nidogen (enactin) | 131390 | NP_002499 |
| Hs.36927 | heat shock 105 kD | | NP_006635 |
| Hs.43666 | protein tyrosine phosphatase type IVA, member 3 | 606449 | NP_116000 |
| Hs.5831 | tissue inhibitor of metalloproteinase 1 (erythroid potentiating activity, collagenase inhibitor) | 305370 | NP_003245 |
| Hs.699 | peptidylprolyl isomerase B (cyclophilin B) | 123841 | NP_000933 |
| Hs.75617 | collagen, type IV, alpha 2 | 120090 | NP_001837 |
| Hs.77890 | guanylate cyclase 1, soluble, beta 3 | 139397 | NP_000848 |
| Hs.78409 | collagen, type XVIII, alpha 1 | 120328 | NP_085059 |
| Hs.78465 | v-jun sarcoma virus 17 oncogene homolog (avian) | 165160 | NP_002219 |
| Hs.821 | Biglycan | 301870 | NP_001702 |
| Hs.82646 | DnaJ (Hsp40) homolog, subfamily B, member 1 | 604572 | NP_006136 |
| Hs.8546 | Notch homolog 3 (*Drosophila*) | 600276 | NP_000426 |

TABLE 4

Markers in Brain and Breast Tumor Epithelium

| Unigene ID | Function | OMIMID | Protein |
|---|---|---|---|
| Hs.107125 | plasmalemma vesicle associated protein | | NP_112600 |
| Hs.111611 | ribosomal protein L27 | 607526 | NP_000979 |
| Hs.111779 | Secreted protein, acidic, cysteine-rich (osteonectin) | 182120 | NP_003109 |
| Hs.119129 | Collagen, type IV, alpha 1 | 120130 | NP_001836 |
| Hs.119571 | Collagen, type III, alpha 1 (Ehlers-Danlos syndrome type IV, autosomal dominant) | 120180 | NP_000081 |
| Hs.125359 | TEM13, Thy-1 cell surface antigen | 188230 | NP_006279 |
| Hs.143897 | Dysferlin, limb girdle muscular dystrophy 2B (autosomal recessive) | 603009 | NP_003485 |
| Hs.151738 | matrix metalloproteinase 9 (gelatinase B, 92 kDa gelatinase, 92 kDa type IV collagenase) | 120361 | NP_004985 |
| Hs.159263 | Collagen, type VI, alpha 2 | 120240 | NP_001840 |
| Hs.172928 | Collagen, type I, alpha 1 | 120150 | NP_000079 |
| Hs.179573 | TEM10, COL1A2 involved in tissue remodeling | 120160 | NP_000080 |
| Hs.211573 | Heparan sulfate proteoglycan 2 (perlecan) | 142461 | NP_005520 |
| Hs.277477 | major histocompatibility complex, class I, C | 142840 | NP_002108 |
| Hs.327412 | *Homo sapiens* clone FLC1492 PRO3121 mRNA, complete cds | | |
| Hs.332173 | transducin-like enhancer of split 2 (E(sp1) homolog, *Drosophila*) | 601041 | NP_003251 |
| Hs.337986 | hypothetical protein MGC4677 | | NP_443103 |
| Hs.365706 | matrix Gla protein | 154870 | NP_000891 |
| Hs.75061 | MARCKS-like protein | 602940 | NP_075385 |
| Hs.75111 | Protease, serine, 11 (IGF binding) | 602194 | NP_002766 |
| Hs.75617 | collagen, type IV, alpha 2 | 120090 | NP_001837 |
| Hs.77961 | major histocompatibility complex, class I, B | 142830 | NP_005505 |
| Hs.79356 | Lysosomal-associated multispanning membrane protein-5 | 601476 | NP_006753 |
| Hs.82085 | serine (or cysteine) proteinase inhibitor, clade E (nexin, plasminogen activator inhibitor type 1), member 1 | 173360 | NP_000593 |
| Hs.821 | Biglycan | 301870 | NP_001702 |

TABLE 5

Breast, Brain, and Colon Tumor Endothelial Markers

| Unigene ID | Function | OMIMID | Protein |
|---|---|---|---|
| Hs.111779 | secreted protein, acidic, cysteine-rich (osteonectin) | 182120 | NP_003109 |
| Hs.119129 | collagen, type IV, alpha 1 | 120130 | NP_001836 |
| Hs.119571 | collagen, type III, alpha 1 (Ehlers-Danlos syndrome type IV, autosomal dominant) | 120180 | NP_000081 |
| Hs.125359 | TEM13, Thy-1 cell surface antigen | 188230 | NP_006279 |
| Hs.151738 | matrix metalloproteinase 9 (gelatinase B, 92 kDa gelatinase, 92 kDa type IV collagenase) | 120361 | NP_004985 |
| Hs.159263 | collagen, type VI, alpha 2 | 120240 | NP_001840 |
| Hs.172928 | collagen, type I, alpha 1 | 120150 | NP_000079 |
| Hs.179573 | TEM10, COL1A2 involved in tissue remodeling | 120160 | NP_000080 |
| Hs.327412 | *Homo sapiens* clone FLC1492 PRO3121 mRNA, complete cds | | |
| Hs.337986 | hypothetical protein MGC4677 | | NP_443103 |
| Hs.75617 | collagen, type IV, alpha 2 | 120090 | NP_001837 |
| Hs.821 | biglycan | 301870 | NP_001702 |

Endothelial cells (ECs) represent only a minor fraction of the total cells within normal or tumor tissues, and only those EC transcripts expressed at the highest levels would be expected to be represented in libraries constructed from unfractionated tissues. The genes described in the current study should therefore provide a valuable resource for basic and clinical studies of human breast angiogenesis in the future.

Isolated and purified nucleic acids, according to the present invention are those which are not linked to those genes to which they are linked in the human genome. Moreover, they are not present in a mixture such as a library containing a multitude of distinct sequences from distinct genes. They may be, however, linked to other genes such as vector sequences or sequences of other genes to which they are not naturally adjacent.

The nucleic acids may represent either the sense or the anti-sense strand. Nucleic acids and proteins although disclosed herein with sequence particularity, may be derived from a single individual. Allelic variants which occur in the population of humans are included within the scope of such nucleic acids and proteins. Those of skill in the art are well able to identify allelic variants as being the same gene or protein. Given a nucleic acid, one of ordinary skill in the art can readily determine an open reading frame present, and consequently the sequence of a polypeptide encoded by the open reading frame and, using techniques well known in the art, express such protein in a suitable host. Proteins comprising such polypeptides can be the naturally occurring proteins, fusion proteins comprising exogenous sequences from other genes from humans or other species, epitope tagged polypeptides, etc. Isolated and purified proteins are not in a cell, and are separated from the normal cellular constituents, such as nucleic acids, lipids, etc. Typically the protein is purified to such an extent that it comprises the predominant species of protein in the composition, such as greater than 50, 60 70, 80, 90, or even 95% of the proteins present.

Using the proteins according to the invention, one of ordinary skill in the art can readily generate antibodies which specifically bind to the proteins. Such antibodies can be monoclonal or polyclonal. They can be chimeric, humanized, or totally human. Any functional fragment or derivative of an antibody can be used including Fab, Fab', Fab2, Fab'2, and single chain variable regions. So long as the fragment or derivative retains specificity of binding for the endothelial marker protein it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

Techniques for making such partially to fully human antibodies are known in the art and any such techniques can be used. According to one particularly preferred embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Nina D. Russel, Jose R. F. Corvalan, Michael L. Gallo, C. Geoffrey Davis, Liise-Anne Pirofski. Production of Protective Human Antipneumococcal Antibodies by Transgenic Mice with Human Immunoglobulin Loci *Infection and Immunity* April 2000, p. 1820-1826; Michael L. Gallo, Vladimir E Ivanov, Aya Jakobovits, and C. Geoffrey Davis. The human immunoglobulin loci introduced into mice: V (D) and J gene segment usage similar to that of adult humans *European Journal of Immunology* 30: 534-540, 2000; Larry L. Green. Antibody engineering via genetic engineering of the mouse: XenoMouse strains are a vehicle for the facile generation of therapeutic human monoclonal antibodies *Journal of Immunological Methods* 231 11-23, 1999; Yang X-D, Corvalan JRF, Wang P, Roy CM-N and Davis C G. Fully Human Anti-interleukin-8 Monoclonal Antibodies: Potential Therapeutics for the Treatment of Inflammatory Disease States. *Journal of Leukocyte Biology* Vol. 66, pp 401-410 (1999); Yang X-D, Jia X-C, Corvalan J R F, Wang P, C G Davis and Jakobovits A. Eradication of Established Tumors by a Fully Human Monoclonal Antibody to the Epidermal Growth Factor Receptor without Concomitant Chemotherapy. *Cancer Research* Vol. 59, Number 6, pp 1236-1243 (1999); Jakobovits A. Production and selection of antigen-specific fully human monoclonal antibodies from mice engineered with human Ig loci. *Advanced Drug Delivery Reviews* Vol. 31, pp: 33-42 (1998); Green L and Jakobovits A. Regulation of B cell development by variable gene complexity in mice reconstituted with human immunoglobulin yeast artificial chromosomes. *J. Exp. Med*. Vol. 188, Number 3, pp: 483-495 (1998); Jakobovits A. The long-awaited magic bullets: therapeutic human monoclonal antibodies from transgenic mice. *Exp. Opin. Invest. Drugs* Vol. 7(4), pp: 607-614 (1998); Tsuda H, Maynard-Currie K, Reid L, Yoshida T, Edamura K, Maeda N, Smithies O, Jakobovits A. Inactivation of Mouse HPRT locus by a 203-bp retrotransposon insertion and a 55-kb gene-targeted deletion: establishment of new HPRT-Deficient mouse embryonic sBEM cell lines. *Genomics* Vol. 42, pp: 413-421 (1997); Sherman-Gold, R. Monoclonal Antibodies: The Evolution from '80s Magic Bullets To Mature, Mainstream Applications as Clinical Therapeutics. *Genetic Engineering News* Vol. 17, Number 14 (August 1997); Mendez M, Green L, Corvalan J, Jia X-C, Maynard-Currie C, Yang X-d, Gallo M, Louie D, Lee D, Erickson K, Luna J, Roy C, Abderrahim H, Kirschenbaum F, Noguchi M, Smith D, Fukushima A, Hales J, Finer M, Davis C, Zsebo K, Jakobovits A. Functional transplant of megabase human immunoglobulin loci recapitulates human antibody response in mice. *Nature Genetics* Vol. 15, pp: 146-156 (1997); Jakobovits A. Mice engineered with human immunoglobulin YACs: A new technology for production of fully human antibodies for autoimmunity therapy. Weir's Handbook of Experimental Immunology, *The Integrated Immune System* Vol. IV, pp: 194.1-194.7 (1996); Jakobovits A. Production of fully human antibodies by transgenic mice. *Current Opinion in Biotechnology* Vol. 6, No. 5, pp: 561-566 (1995); Mendez M, Abderrahim H, Noguchi M, David N, Hardy M, Green L, Tsuda H, Yoast S, Maynard-Currie C, Garza D, BEMmill R, Jakobovits A, Klapholz S. Analysis of the structural integrity of YACs comprising human immunoglobulin genes in yeast and in embryonic sBEM cells. *Genomics* Vol. 26, pp: 294-307 (1995); Jakobovits A. YAC Vectors: Humanizing the mouse genome. *Current Biology* Vol. 4, No. 8, pp: 761-763 (1994); Arbones M, Ord D, Ley K, Ratech H, Maynard-Curry K, Otten G, Capon D, Tedder T. Lymphocyte homing and leukocyte rolling and migration are impaired in L-selectin-deficient mice. *Immunity* Vol. 1, No. 4, pp: 247-260 (1994); Green L, Hardy M, Maynard-Curry K, Tsuda H, Louie D, Mendez M, Abderrahim H, Noguchi M, Smith D, Zeng Y, et. al. Antigen-specific human monoclonal antibodies from mice engineered with human Ig heavy and light chain YACs. *Nature Genetics* Vol. 7, No. 1, pp: 13-21 (1994); Jakobovits A, Moore A, Green L, Vergara G, Maynard-Curry K, Austin H, Klapholz S. Germ-line transmission and expression of a human-derived yeast artificial chromosome. *Nature* Vol. 362, No. 6417, pp: 255-258 (1993); Jakobovits A, Vergara G, Kennedy J, Hales J, McGuinness R, Casentini-Borocz D, Brenner D, Otten G. Analysis of homozygous mutant chimeric mice: deletion of the immunoglobulin heavy-chain joining region blocks B-cell development and antibody production. *Proceedings of the National Academy of Sciences USA* Vol. 90, No. 6, pp: 2551-2555 (1993); Kucherlapati et al., U.S. Pat. No. 6,1075,181.

Antibodies can also be made using phage display techniques. Such techniques can be used to isolate an initial antibody or to generate variants with altered specificity or avidity characteristics. Single chain Fv can also be used as is convenient. They can be made from vaccinated transgenic mice, if desired. Antibodies can be produced in cell culture, in phage, or in various animals, including but not limited to cows, rabbits, goats, mice, rats, hamsters, guinea pigs, sheep, dogs, cats, monkeys, chimpanzees, apes.

Antibodies can be labeled with a detectable moiety such as a radioactive atom, a chromophore, a fluorophore, or the like.

Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I) yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing antitumor agents (e.g., antisense oligonucleotides, plasmids which encode for toxins, methotrexate, etc.); and other antibodies or antibody fragments, such as F(ab).

Those of skill in the art will readily understand and be able to make such antibody derivatives, as they are well known in the art. The antibodies may be cytotoxic on their own, or they may be used to deliver cytotoxic agents to particular locations in the body. The antibodies can be administered to individuals in need thereof as a form of passive immunization.

Characterization of extracellular regions for the cell surface and secreted proteins from the protein sequence is based on the prediction of signal sequence, transmembrane domains and functional domains. Antibodies are preferably specifically immunoreactive with membrane associated proteins, particularly to extracellular domains of such proteins or to secreted proteins. Such targets are readily accessible to antibodies, which typically do not have access to the interior of cells or nuclei. However, in some applications, antibodies directed to intracellular proteins may be useful as well. Moreover, for diagnostic purposes, an intracellular protein may be an equally good target since cell lysates may be used rather than a whole cell assay.

Computer programs can be used to identify extracellular domains of proteins whose sequences are known. Such programs include SMART software (Schultz et al., Proc. Natl. Acad. Sci. USA 95: 5857-5864, 1998) and Pfam software (BaBEMan et al., Nucleic acids Res. 28: 263-266, 2000) as well as PSORTII. Typically such programs identify transmembrane domains; the extracellular domains are identified as immediately adjacent to the transmembrane domains. Prediction of extracellular regions and the signal cleavage sites are only approximate. It may have a margin of error + or −5 residues. Signal sequence can be predicted using three different methods (Nielsen et al, *Protein Engineering* 10: 1-6, 1997, Jagla et. al, Bioinformatics 16: 245-250, 2000, Nakai, K and Horton, P. Trends in Biochem. Sci. 24:34-35, 1999) for greater accuracy. Similarly transmembrane (TM) domains can be identified by multiple prediction methods. (Pasquier, et. al, Protein Eng. 12:381-385, 1999, Sonnhammer et al., In Proc. of Sixth Int. Conf. on Intelligent Systems for Molecular Biology, p. 175-182, Ed J. Glasgow, T. Littlejohn, F. Major, R. Lathrop, D. Sankoff, and C. Sensen Menlo Park, Calif.: AAAI Press, 1998, Klein, et. al, Biochim. Biophys. Acta, 815:468, 1985, Nakai and Kanehisa Genomics, 14: 897-911, 1992). In ambiguous cases, locations of functional domains in well characterized proteins are used as a guide to assign a cellular localization.

Putative functions or functional domains of novel proteins can be inferred from homologous regions in the database identified by BLAST searches (Altschul et. al. Nucleic Acid Res. 25: 3389-3402, 1997) and/or from a conserved domain database such as Pfam (BaBEMan et. al, Nucleic Acids Res. 27:260-262 1999) BLOCKS (Henikoff, et. al, Nucl. Acids Res. 28:228-230, 2000) and SMART (Ponting, et. al, Nucleic Acid Res. 27,229-232, 1999). Extracellular domains include regions adjacent to a transmembrane domain in a single transmembrane domain protein (out-in or type I class). For multiple transmembrane domains proteins, the extracellular domain also includes those regions between two adjacent transmembrane domains (in-out and out-in). For type II transmembrane domain proteins, for which the N-terminal region is cytoplasmic, regions following the transmembrane domain is generally extracellular. Secreted proteins on the other hand do not have a transmembrane domain and hence the whole protein is considered as extracellular.

Membrane associated proteins can be engineered to delete the transmembrane domains, thus leaving the extracellular portions which can bind to ligands. Such soluble forms of transmembrane receptor proteins can be used to compete with natural forms for binding to ligand. Thus such soluble forms act as inhibitors and can be used therapeutically as anti-angiogenic agents, as diagnostic tools for the quantification of natural ligands, and in assays for the identification of small molecules which modulate or mimic the activity of a BEM: ligand complex.

Alternatively, the endothelial markers themselves can be used as vaccines to raise an immune response in the vaccinated animal or human. For such uses, a protein, or immunogenic fragment of such protein, corresponding to the intracellular, extracellular or secreted BEM of interest is administered to a subject. The immogenic agent may be provided as a purified preparation or in an appropriately expressing cell. The administration may be direct, by the delivery of the immunogenic agent to the subject, or indirect, through the delivery of a nucleic acid encoding the immunogenic agent under conditions resulting in the expression of the immunogenic agent of interest in the subject. The BEM of interest may be delivered in an expressing cell, such as a purified population of breast tumor endothelial cells or a population of fused breast tumor endothelial and dendritic cells. Nucleic acids encoding the BEM of interest may be delivered in a viral or non-viral delivery vector or vehicle. Non-human sequences encoding the human BEM of interest or other mammalian homolog can be used to induce the desired immunologic response in a human subject. For several of the BEMs of the present invention, mouse, rat or other ortholog sequences can be obtained from the literature or using techniques well within the skill of the art.

Endothelial cells can be identified using the markers which are disclosed herein as being endothelial cell specific. Antibodies specific for such markers can be used to identify such cells, by contacting the antibodies with a population of cells containing some endothelial cells. The presence of cross-reactive material with the antibodies identifies particular cells as endothelial. Similarly, lysates of cells can be tested for the presence of cross-reactive material. Any known format or technique for detecting cross-reactive material can be used including, immunoblots, radioimmunoassay, ELISA, immunoprecipitation, and immunohistochemistry. In addition, nucleic acid probes for these markers can also be used to identify endothelial cells. Any hybridization technique known in the art including Northern blotting, RT-PCR, microarray hybridization, and in situ hybridization can be used.

One can identify breast tumor endothelial cells for diagnostic purposes, testing cells suspected of containing one or more BEMs. One can test both tissues and bodily fluids of a subject. For example, one can test a patient's blood for evidence of intracellular and membrane associated BEMs, as well as for secreted BEMs. Of particular interest in this context is the testing of breast duct fluid. Intracellular and/or membrane associated BEMs may be present in bodily fluids as the result of high levels of expression of these factors and/or through lysis of cells expressing the BEMs.

Populations of various types of endothelial cells can also be made using the antibodies to endothelial markers of the invention. The antibodies can be used to purify cell populations according to any technique known in the art, including but not limited to fluorescence activated cell sorting. Such techniques permit the isolation of populations which are at least 50, 60, 70, 80, 90, 92, 94, 95, 96, 97, 98, and even 99% the type of endothelial cell desired, whether normal, tumor, or pan-endothelial. Antibodies can be used to both positively select and negatively select such populations. Preferably at least 1, 5, 10, 15, 20, or 25 of the appropriate markers are expressed by the endothelial cell population.

Populations of endothelial cells made as described herein, can be used for screening drugs to identify those suitable for inhibiting the growth of tumors by virtue of inhibiting the growth of the tumor vasculature.

Populations of endothelial cells made as described herein, can be used for screening candidate drugs to identify those suitable for modulating angiogenesis, such as for inhibiting the growth of tumors by virtue of inhibiting the growth of endothelial cells, such as inhibiting the growth of the tumor or other undesired vasculature, or alternatively, to promote the growth of endothelial cells and thus stimulate the growth of new or additional large vessel or microvasculature.

Inhibiting the growth of endothelial cells means either regression of vasculature which is already present, or the slowing or the absence of the development of new vascularization in a treated system as compared with a control system. By stimulating the growth of endothelial cells, one can influence development of new (neovascularization) or additional vasculature development (revascularization). A variety of model screening systems are available in which to test the angiogenic and/or anti-angiogenic properties of a given candidate drug. Typical tests involve assays measuring the endothelial cell response, such as proliferation, migration, differentiation and/or intracellular interaction with a given candidate drug. By such tests, one can study the signals and effects of the test stimuli. Some common screens involve measurement of the inhibition of heparanase, endothelial tube formation on Matrigel, scratch induced motility of endothelial cells, platelet-derived growth factor driven proliferation of vascular smooth muscle cells, and the rat aortic ring assay (which provides an advantage of capillary formation rather than just one cell type).

Drugs can be screened for the ability to mimic or modulate, inhibit or stimulate, growth of tumor endothelium cells and/or normal endothelial cells. Drugs can be screened for the ability to inhibit tumor endothelium growth but not normal endothelium growth or survival. Similarly, human cell populations, such as normal endothelium populations or breast tumor endothelial cell populations, can be contacted with test substances and the expression of breast tumor endothelial markers and/or normal endothelial markers determined. Test substances that decrease the expression of breast tumor endothelial markers (BEMs) are candidates for inhibiting angiogenesis and the growth of tumors. In cases where the activity of a BEM is known, agents can be screened for their ability to decrease or increase the activity.

For those breast tumor endothelial markers identified as containing transmembrane regions, it is desirable to identify drug candidates capable of binding to the BEM receptors found at the cell surface. For some applications, the identification of drug candidates capable of blocking the BEM receptor from its native ligand will be desired. For some applications, the identification of a drug candidate capable of binding to the BEM receptor may be used as a means to deliver a therapeutic or diagnostic agent. For other applications, the identification of drug candidates capable of mimicking the activity of the native ligand will be desired. Thus, by manipulating the binding of a transmembrane BEM receptor:ligand complex, one may be able to promote or inhibit further development of endothelial cells and hence, vascularization.

For those breast tumor endothelial markers identified as being secreted proteins, i.e., extracellular, it is desirable to identify drug candidates capable of binding to the secreted BEM protein. For some applications, the identification of drug candidates capable of interfering with the binding of the secreted BEM it is native receptor. For other applications, the identification of drug candidates capable of mimicking the activity of the native receptor will be desired. Thus, by manipulating the binding of the secreted BEM:receptor complex, one may be able to promote or inhibit further development of endothelial cells, and hence, vascularization.

Expression can be monitored according to any convenient method. Protein or mRNA can be monitored. Any technique known in the art for monitoring specific genes' expression can be used, including but not limited to ELISAs, SAGE, microarray hybridization, Western blots. Changes in expression of a single marker may be used as a criterion for significant effect as a potential pro-angiogenic, anti-angiogenic or anti-tumor agent. However, it also may be desirable to screen for test substances that are able to modulate the expression of at least 5, 10, 15, or 20 of the relevant markers, such as the tumor or normal endothelial markers. Inhibition of BEM protein activity can also be used as a drug screen.

Test substances for screening can come from any source. They can be libraries of natural products, combinatorial chemical libraries, biological products made by recombinant libraries, etc. The source of the test substances is not critical to the invention. The present invention provides means for screening compounds and compositions that may previously have been overlooked in other screening schemes. Nucleic acids and the corresponding encoded proteins of the markers of the present invention can be used therapeutically in a variety of modes. BEMs can be used to stimulate the growth of vasculature, such as for wound healing or to circumvent a blocked vessel. The nucleic acids and encoded proteins can be administered by any means known in the art. Such methods include, using liposomes, nanospheres, viral vectors, non-viral vectors comprising polycations, etc. Suitable viral vectors include adenovirus, retroviruses, and sindbis virus. Administration modes can be any known in the art, including parenteral, intravenous, intramuscular, intraperitoneal, topical, intranasal, intrarectal, intrabronchial, etc.

Specific biological antagonists of BEMs can also be used to therapeutic benefit. For example, antibodies, T cells specific for a BEM, antisense to a BEM, interference RNA to a BEM, and ribozymes specific for a BEM can be used to restrict, inhibit, reduce, and/or diminish tumor or other abnormal or undesirable vasculature growth. Such antagonists can be administered as is known in the art for these classes of antagonists generally. Anti-angiogenic drugs and agents can be used to inhibit tumor growth, as well as to treat diabetic retinopathy, rheumatoid arthritis, psoriasis, polycystic kidney disease (PKD), and other diseases requiring angiogenesis for their pathologies.

Mouse counterparts to human BEMs can be used in mouse cancer models or in cell lines or in vitro to evaluate potential anti-angiogenic or anti-tumor compounds or therapies. Their expression can be monitored as an indication of effect. Mouse BEMs can be used as antigens for raising antibodies which can be tested in mouse tumor models. Mouse BEMs with transmembrane domains are particularly preferred for this purpose. Mouse BEMs can also be ued as vaccines to raise an immunological response in a human to the human ortholog.

The above disclosure generally describes the present invention. All references disclosed herein are expressly incorporated by reference in their entireties. A more complete understanding can be obtained by reference to the following specific examples which are provided herein for purposes of illustration only, and are not intended to limit the scope of the invention.

Example 1

Function of BEM proteins was determined using bioinformatics tools. BEMs that are putative functional receptors with short cytoplasmic tails make particularly interesting targets.

| Breast Tumor Endothelial Putative Functional Receptors with Short Cytoplasmic Tails | | | |
|---|---|---|---|
| Unigene ID | Function | OMIMID | Protein |
| Hs.181418 | KIAA0152 gene product | — | 055545 |
| Hs.25691 | receptor (calcitonin) activity modifying protein 3 | 605155 | 005847 |
| Hs.9598 | sema domain | — | BAB212835 |

Example 2

Protein kinases were identified among the BEMs. These are particularly good druggable targets, especially for small molecules.

| Protein Kinases | | | |
|---|---|---|---|
| Unigene ID | Function | OMIMID | Protein |
| Hs.100009 | cyclin-dependent kinase 3 | 123828 | |
| Hs.143897 | dysferlin, limb girdle muscular dystrophy 2B (autosomal recessive) | 603009 | NP_003485 |
| Hs.184367 | Ca2+-promoted Ras inactivator | | BAA25464 |
| Hs.246857 | mitogen-activated protein kinase 9 | 602896 | NP_620708 |
| Hs.75087 | FAST kinase | 606965 | NP-079372 |
| Hs.296323 | serum/glucocorticoid regulated kinase | 602958 | NP_005618 |
| Hs.246857 | mitogen-activated protein kinase | 602986 | NP_620708 |

Example 3

Kinases with non-protein substrates were also identified. These similarly are believed to be exceedingly good druggable targets.

| Kinases with non-protein substrates | | | |
|---|---|---|---|
| Unigene ID | Function | OMIMID | Protein |
| Hs.118625 | hexokinase 1 | 142600 | NP_277035 |
| Hs.82689 | tumor rejection antigen (gp96) 1 | 191175 | NP_003290 |

Example 4

Growth factors were identified among the BEMs:

| Growth factors | | | |
|---|---|---|---|
| Unigene ID | Function | OMIMID | Protein |
| Hs.91143 | jagged 1 (Alagille syndrome) | 601920 | NP_000205 |
| Hs.119206 | insulin-like growth factor binding protein 7 | 602867 | NP_001544 |
| Hs.1516 | insulin-like growth factor binding protein 4 | 146733 | NP_001543 |
| Hs.211573 | heparan sulfate proteoglycan 2 (perlecan) | 142461 | NP_005520 |
| Hs.75111 | protease, serine, 11 (IGF binding) | 602194 | NP_002766 |
| Hs.8546 | Notch homolog 3 (*Drosophila*) | 600276 | NP_000426 |

Example 5

Phosphatases, like kinases, are readily amenable to screening for inhibitors, especially small molecule inhibitors:

| Phosphatases | | | |
|---|---|---|---|
| Unigene ID | Function | OMIMID | Protein |
| Hs.8997 | heat shock 70 kDa protein 1A/1B [*Homo sapiens*] | 140550 | NP_005336 |
| Hs.205353 | ectonucleoside triphosphate diphosphohydrolase 1 isoform 1 [*Homo sapiens*] | 601752 | NP_001767 |
| Hs.43666 | protein tyrosine phosphatase type IVA 3 isoform 1 [*Homo sapiens*] | 606449 | NP_116000 |
| Hs.6147 | tensin-like C1 domain-containing phosphatase isoform 1 [*Homo sapiens*] | — | NP_056134 |

Example 6

GPCRs were identified among the BEMs:

| GPCRs | | | |
|---|---|---|---|
| Unigene ID | Function | OMIMID | Protein |
| Hs.17170 | G protein-coupled receptor 4 | 600551 | NP_005273 |

Example 7

The cellular location of the BEMs was determined to be either cytoplasmic, etracellular, membrane, or nuclear, as shown below.

Extracellular Proteins

| Unigene ID | Function | OMIMID | Protein |
|---|---|---|---|
| Hs.75415 | Beta-2-microglobulin | 109700 | NP_004039 |
| Hs.821 | Biglycan | 301870 | NP_001702 |
| Hs.172928 | collagen, type I, alpha 1 | 120150 | NP_000079 |
| Hs.119571 | collagen, type III, alpha 1 (Ehlers-Danlos syndrome type IV, autosomal dominant) | 120180 | NP_000081 |
| Hs.119129 | collagen, type IV, alpha 1 | 120130 | NP_001836 |
| Hs.75617 | collagen, type IV, alpha 2 | 120090 | NP_001837 |
| Hs.235368 | collagen, type V, alpha 3 | 120216 | NP_056534 |
| Hs.159263 | collagen, type VI, alpha 2 | 120240 | NP_001840 |
| Hs.78409 | collagen, type XVIII, alpha 1 | 120328 | NP_085059 |
| Hs.278625 | complement component 4B | 120820 | NP_000583 |
| Hs.230 | Fibromodulin | 600245 | NP_002014 |
| Hs.211573 | heparan sulfate proteoglycan 2 (perlecan) | 142461 | NP_005520 |
| Hs.1516 | insulin-like growth factor binding protein 4 | 146733 | NP_001543 |
| Hs.119206 | insulin-like growth factor binding protein 7 | 602867 | NP_001544 |
| Hs.49215 | integrin-binding sialoprotein (bone sialoprotein, bone sialoprotein II) | 147563 | NP_004958 |
| Hs.79339 | lectin, galactoside-binding, soluble, 3 binding protein | 600626 | NP_005558 |
| Hs.106747 | likely homolog of rat and mouse retinoid-inducible serine carboxypeptidase | | NP_067639 |
| Hs.365706 | matrix Gla protein | 154870 | NP_000891 |
| Hs.151738 | matrix metalloproteinase 9 (gelatinase B, 92 kDa gelatinase, 92 kDa type IV collagenase) | 120361 | NP_004985 |
| Hs.699 | peptidylprolyl isomerase B (cyclophilin B) | 123841 | NP_000933 |
| Hs.75111 | protease, serine, 11 (IGF binding) | 602194 | NP_002766 |
| Hs.25338 | protease, serine, 23 | | |
| Hs.78224 | ribonuclease, RNase A family, 1 (pancreatic) | 180440 | AAH05324 |
| Hs.111779 | secreted protein, acidic, cysteine-rich (osteonectin) | 182120 | NP_003109 |
| Hs.82085 | serine (or cysteine) proteinase inhibitor, clade E (nexin, plasminogen activator inhibitor type 1), member 1 | 173360 | NP_000593 |
| Hs.179573 | TEM10, COL1A2 involved in tissue remodeling | 120160 | NP_000080 |
| Hs.356624 | TEM11, nidogen (enactin) | 131390 | NP_002499 |
| Hs.5831 | tissue inhibitor of metalloproteinase 1 (erythroid potentiating activity, collagenase inhibitor) | 305370 | NP_003245 |
| Hs.82689 | tumor rejection antigen (gp96) 1 | 191175 | NP_003290 |

Membrane Proteins

| Unigene ID | Function | Protein | TM Domains | TM Location | Orientation of N-terminus |
|---|---|---|---|---|---|
| Hs.202 | benzodiazapine receptor (peripheral) | NP_000705 | 3 | 107-129, 78-100, 133-155 | OUT |
| Hs.76206 | cadherin 5, type 2, VE-cadherin (vascular epithelium) | NP_001786 | 1 | 598-620 | Unsure |
| Hs.122359 | calcium channel, voltage-dependent, alpha 1H subunit | NP_066921 | 19 | 1370-1392, 1614-1636, 1533-1555, 141-163, 915-937, 396-418, 1651-1673, 1745-1767, 990-1012, 234-256, 1430-1452, 1333-1355, 1680-1702, 855-877, 1295-1316, 826-848, 100-122, 1840-1862, 364-386 | IN |
| Hs.84298 | CD74 antigen (invariant polypeptide of major histocompatibility complex, class II antigen-associated) | NP_004346 | 1 | 49-71 | IN |
| Hs.1244 | CD9 antigen (p24) | NP_001760 | 4 | 59-81, 88-110, 12-34, 194-216 | IN |
| Hs.143897 | dysferlin, limb girdle muscular dystrophy 2B (autosomal recessive) | NP_003485 | 1 | 2045-2067 | Unsure |
| Hs.205353 | ectonucleoside triphosphate diphosphohydrolase 1 | NP_001767 | 1 | 477-499 | IN |
| Hs.17170 | G protein-coupled receptor 4 | NP_005273 | 5 | 55-77, 92-113, 20-42, 225-244, 183-205 | OUT |

-continued

Membrane Proteins

| Unigene ID | Function | Protein | TM Domains | TM Location | Orientation of N-terminus |
|---|---|---|---|---|---|
| Hs.25549 | hypothetical protein FLJ20898 | NP_078876 | 3 | 102-124, 139-161, 168-190 | Unsure |
| Hs.277704 | hypoxia up-regulated 1 | NP_006380 | 1 | 13-35 | IN |
| Hs.76095 | Immediate early response 3 | NP_434702 | 1 | 123-145 | Unsure |
| Hs.265827 | interferon, alpha-inducible protein (clone IFI-6-16) | NP_075011 | 2 | 5-24, 44-66 | IN |
| Hs.91143 | jagged 1 (Alagille syndrome) | NP_000205 | 1 | 1069-1091 | Unsure |
| Hs.181418 | KIAA0152 gene product | NP_055545 | 1 | 271-290 | OUT |
| Hs.79356 | Lysosomal-associated multispanning membrane protein-5 | NP_006753 | 5 | 63-85, 100-121, 142-164, 15-37, 184-206 | Unsure |
| Hs.77961 | major histocompatibility complex, class I, B | NP_005505 | 1 | 308-330 | OUT |
| Hs.277477 | major histocompatibility complex, class I, C | NP_002108 | 1 | 308-330 | OUT |
| Hs.110024 | NADH:ubiquinone oxidoreductase MLRQ subunit homolog | NP_064527 | 1 | 20-42 | Unsure |
| Hs.8546 | Notch homolog 3 (*Drosophila*) | NP_000426 | 3 | 1641-1663, 1496-1518, 20-42 | Unsure |
| Hs.107125 | plasmalemma vesicle associated protein | NP_112600 | 1 | 42-64 | IN |
| Hs.83974 | solute carrier family 21 (prostaglandin transporter), member 2 | NP_005621 | 12 | 256-278, 363-385, 397-419, 100-122, 208-230, 326-348, 173-195, 514-536, 71-93, 557-576, 606-628, 25-47 | Unsure |
| Hs.125359 | TEM13, Thy-1 cell surface antigen | NP_006279 | 1 | 140-161 | Unsure |
| Hs.125036 | TEM17 | NP_065138 | 1 | 425-447 | OUT |
| Hs.9598 | sema domain, immunoglobulin domain (Ig) | BAB21836 | 1 | 727-794 | OUT |
| Hs.202 | Benzodiazapine receptor (peripheral)-mitochondrial | NP_00715 | 3 | 107-129, 78-100, 133-155 | OUT |

Nuclear Proteins

| Unigene ID | Function | OMIMID | Protein |
|---|---|---|---|
| Hs.244 | amino-terminal enhancer of split | 600188 | |
| Hs.154029 | bHLH factor Hes4 | | NP_066993 |
| Hs.75450 | delta sleep inducing peptide, immunoreactor | 602960 | |
| Hs.75087 | FAST kinase | 606965 | NP_079372 |
| Hs.356668 | guanine nucleotide binding protein (G protein), gamma 5 | 600874 | NP_005265 |
| Hs.406410 | H19, imprinted maternally expressed untranslated mRNA | 103280 | BAB71280 |
| Hs.234434 | hairy/enhancer-of-split related with YRPW motif 1 | 602953 | NP_036390 |
| Hs.23823 | hairy/enhancer-of-split related with YRPW motif-like | | NP_055386 |
| Hs.15265 | heterogeneous nuclear ribonucleoprotein R | 607201 | NP_005817 |
| Hs.8728 | hypothetical protein DKFZp434G171 | | CAB61365 |
| Hs.240170 | hypothetical protein MGC2731 | | NP_076973 |
| Hs.146360 | hypothetical protein MGC34648 | | NP_689873 |
| Hs.337986 | hypothetical protein MGC4677 | | NP_443103 |
| Hs.197540 | hypoxia-inducible factor 1, alpha subunit (basic helix-loop-helix transcription factor) | 603348 | NP_001521 |
| Hs.75061 | MARCKS-like protein | 602940 | NP_075385 |
| Hs.246857 | mitogen-activated protein kinase 9 | 602896 | NP_620708 |
| Hs.79110 | Nucleolin | 164035 | NP_005372 |
| Hs.298229 | prefoldin 2 | | NP_036526 |
| Hs.250655 | prothymosin, alpha (gene sequence 28) | 188390 | NP_002814 |
| Hs.24950 | regulator of G-protein signalling 5 | 603276 | NP_003608 |
| Hs.76640 | RGC32 protein | | |
| Hs.3109 | Rho GTPase activating protein 4 | 300023 | NP_001657 |
| Hs.337445 | ribosomal protein L37 | 604181 | NP_000988 |
| Hs.197114 | serine/arginine repetitive matrix 2 | 606032 | NP_057417 |
| Hs.48029 | snail homolog 1 (*Drosophila*) | 604238 | NP_005976 |
| Hs.168357 | T-box 2 | 600747 | NP_005985 |
| Hs.332173 | transducin-like enhancer of split 2 (E(sp1) homolog, *Drosophila*) | 601041 | NP_003251 |
| Hs.78465 | v-jun sarcoma virus 17 oncogene homolog (avian) | 165160 | NP_002219 |

Cytoplasmic proteins

| Unigene ID | Function | OMIMID | Protein |
|---|---|---|---|
| Hs.184367 | Ca2+-promoted Ras inactivator | | BAA25464 |
| Hs.2575 | calpain 1, (mu/l) large subunit | 114220 | NP_005177 |
| Hs.100009 | cyclin-dependent kinase 3 | 123828 | |
| Hs.31053 | cytoskeleton-associated protein 1 | 601303 | NP_001272 |
| Hs.82646 | DnaJ (Hsp40) homolog, subfamily B, member 1 | 604572 | NP_006136 |
| Hs.169476 | glyceraldehyde-3-phosphate dehydrogenase | 138400 | NP_002037 |
| Hs.77890 | guanylate cyclase 1, soluble, beta 3 | 139397 | NP_000848 |
| Hs.36927 | heat shock 105 Kd | | NP_006635 |

-continued

Cytoplasmic proteins

| Unigene ID | Function | OMIMID | Protein |
|---|---|---|---|
| Hs.1197 | heat shock 10 kDa protein 1 (chaperonin 10) | 600141 | NP_002148 |
| Hs.8997 | heat shock 70 kDa protein 1A | 140550 | NP_005336 |
| Hs.180414 | heat shock 70 kDa protein 8 | 600816 | NP_006588 |
| Hs.118625 | hexokinase 1 | 142600 | NP_277035 |
| Hs.327412 | Homo sapiens clone FLC1492 PRO3121 mRNA, complete cds | | |
| Hs.833 | interferon, alpha-inducible protein (clone IFI-15K) | 147571 | NP_005092 |
| Hs.150580 | putative translation initiation factor | | NP_005792 |
| Hs.173737 | ras-related C3 botulinum toxin substrate 1 (rho family, small GTP binding protein Rac1) | 602048 | |
| Hs.119122 | ribosomal protein L13a | | |
| Hs.111611 | ribosomal protein L27 | 607526 | NP_000979 |
| Hs.177592 | ribosomal protein, large, P1 | 180520 | |
| Hs.12956 | Tax interaction protein 1 | | NP_055419 |
| Hs.251653 | tubulin, beta, 2 | 602660 | NP_006079 |

REFERENCES

Abounader, R., Lal, B., Luddy, C., Koe, G., Davidson, B., Rosen, E. M., and Laterra, J. (2002). In vivo targeting of SF/HGF and c-met expression via U1snRNA/ribozymes inhibits breast tumor growth and angiogenesis and promotes apoptosis. Faseb J 16, 108-10.

Bart, J., Groen, H. J., Hendrikse, N. H., van der Graaf, W. T., Vaalburg, W., and de Vries, E. G. (2000). The blood-brain barrier and oncology: new insights into function and modulation. Cancer Treat Rev 26, 449-62.

Bernsen, H. J., Rijken, P. F., Oostendorp, T., and van der Kogel, A. J. (1995). Vascularity and perfusion of human breast tumors xenografted in the athymic nude mouse. Br J Cancer 71, 721-6.

Bowers, D. C., Fan, S., Walter, K. A., Abounader, R., Williams, J. A., Rosen, E. M., and Laterra, J. (2000). Scatter factor/hepatocyte growth factor protects against cytotoxic death in human glioblastoma via phosphatidylinositol 3-kinase- and AKT-dependent pathways. Cancer Res 60, 4277-83.

Chen, H., Centola, M., Altschul, S. F., and Metzger, H. (1998). Characterization of gene expression in resting and activated mast cells. J Exp Med 188, 1657-68.

Guerin, C., Wolff, J. E., Laterra, J., Drewes, L. R., Brem, H., and Goldstein, G. W. (1992). Vascular differentiation and glucose transporter expression in rat breast tumors: effects of steroids. Ann Neurol 31, 481-7.

Hobbs, S. K., Monsky, W. L., Yuan, F., Roberts, W. G., Griffith, L., Torchilin, V. P., and Jain, R. K. (1998). Regulation of transport pathways in tumor vessels: role of tumor type and microenvironment. Proc Natl Acad Sci USA 95, 4607-12.

Holash, J., Maisonpierre, P. C., Compton, D., Boland, P., Alexander, C. R., Zagzag, D., Yancopoulos, G. D., and Wiegand, S. J. (1999). Vessel cooption, regression, and growth in tumors mediated by angiopoietins and VEGF. Science 284, 1994-8.

Huminiecki, L., and Bicknell, R. (2000). In silico cloning of novel endothelial-specific genes. Genome Res 10, 1796-806.

Lamszus, K., Laterra, J., Westphal, M., and Rosen, E. M. (1999). Scatter factor/hepatocyte growth factor (SF/HGF) content and function in human breast tumors. Int J Dev Neurosci 17, 517-30.

Marx, J. (2001). Caveolae: a once-elusive structure gets some respect. Science 294, 1862-5.

Roberts, W. G., and Palade, G. E. (1997). Neovasculature induced by vascular endothelial growth factor is fenestrated. Cancer Res 57, 765-72.

Shinoura, N., Shamraj, 0.1., Hugenholz, H., Zhu, J. G., McBlack, P., Warrick, R., Tew, J. J., Wani, M. A., and Menon, A. G. (1995). Identification and partial sequence of a cDNA that is differentially expressed in human brain tumors. Cancer Lett 89, 215-21.

Smith, R. M., Jarret, L. (1988). Lab. Invest. 58, 613-629.

St Croix, B., Rago, C., Velculescu, V., Traverso, G., Romans, K. E., Montgomery, E., Lal, A., Riggins, G. J., Lengauer, C., Vogelstein, B., and Kinzler, K. W. (2000). Genes expressed in human tumor endothelium. Science 289, 1197-202.

Stan, R. V., Arden, K. C., and Palade, G. E. (2001). cDNA and protein sequence, genomic organization, and analysis of cis regulatory elements of mouse and human PLVAP genes. Genomics 72, 304-13.

Tamagnone, L., Artigiani, S., Chen, H., He, Z., Ming, G. I., Song, H., Chedotal, A., Winberg, M. L., Goodman, C. S., Poo, M., Tessier-Lavigne, M., and Comoglio, P. M. (1999). Plexins are a large family of receptors for transmembrane, secreted, and GPI-anchored semaphorins in vertebrates. Cell 99, 71-80.

Vajkoczy, P., and Menger, M. D. (2000). Vascular microenvironment in breast tumors. J Neurooncol 50, 99-108.

Vajkoczy, P., Schilling, L., Ullrich, A., Schmiedek, P., and Menger, M. D. (1998). Characterization of angiogenesis and microcirculation of high-grade breast tumor: an intravital multifluorescence microscopic approach in the athymic nude mouse. J Cereb Blood Flow Metab 18, 510-20.

Vick, N. A., and Bigner, D. D. (1972). Microvascular abnormalities in virally-induced canine BREAST tumors. Structural bases for altered blood-brain barrier function. J Neurol Sci 17, 29-39.

We claim:

1. A method to aid in diagnosing breast tumor, comprising the steps of:
    detecting an expression product of at least one gene in a first breast tissue sample suspected of being neoplastic wherein said one gene is snail homolog 1 (*Drosophila*);
    comparing expression of the at least one gene in the first breast tissue sample with expression of the at least one gene in a second breast tissue sample which is normal and
    identifying the first breast tissue sample as likely to be neoplastic when expression of the one gene in the first breast tissue sample is increased relative to the second tissue sample.

2. The method of claim 1 wherein the increased expression of the at least one gene in the first breast tissue sample relative to the second tissue sample is at least two-fold higher.

3. The method of claim 1 wherein the increased expression of the at least one gene in the first breast tissue sample relative to the second tissue sample is at least five-fold higher.

4. The method of claim 1 wherein the increased expression of the at least one gene in the first breast tissue sample relative to the second tissue sample is at least ten-fold higher.

5. The method of claim 1 wherein the expression product is RNA.

6. The method of claim 1 wherein the expression product is protein.

7. The method of claim 1 wherein the first and second tissue samples are from a human.

8. The method of claim 1 wherein the first and second tissue samples are from the same human.

9. The method of claim 1 wherein the step of detecting is performed using a Western blot.

10. The method of claim 1 wherein the step of detecting is performed using an immunoassay.

11. The method of claim 1 wherein the step of detecting is performed using an immunohistochemical assay.

12. The method of claim 1 wherein the step of detecting is performed using SAGE.

13. The method of claim 1 wherein the step of detecting is performed using hybridization to a microarray.

* * * * *